(12) United States Patent
Hadwiger et al.

(10) Patent No.: US 7,994,307 B2
(45) Date of Patent: Aug. 9, 2011

(54) RNAI MODULATION OF THE BCR-ABL FUSION GENE AND USES THEREOF

(75) Inventors: Philipp Hadwiger, Altenkunstadt (DE); Hans-Peter Vornlocher, Bayreuth (DE); Heiko Van Der Kuip, Ammerbuch (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/510,128

(22) Filed: Jul. 27, 2009

(65) Prior Publication Data

US 2010/0234446 A1    Sep. 16, 2010

Related U.S. Application Data

(60) Division of application No. 12/171,291, filed on Jul. 10, 2008, now abandoned, which is a continuation of application No. 11/286,624, filed on Nov. 23, 2005, now abandoned.

(60) Provisional application No. 60/632,403, filed on Dec. 1, 2004, provisional application No. 60/630,878, filed on Nov. 24, 2004.

(51) Int. Cl.
*C07H 21/04* (2006.01)
*C07H 21/02* (2006.01)
*A61K 48/00* (2006.01)

(52) U.S. Cl. .................. 536/24.5; 536/23.1; 514/44

(58) Field of Classification Search .................. None
See application file for complete search history.

(56) References Cited

U.S. PATENT DOCUMENTS

| | | | |
|---|---|---|---|
| 5,328,470 A | 7/1994 | Nabel et al. | |
| 5,652,222 A * | 7/1997 | Calabretta et al. | 514/44 A |
| 6,107,094 A | 8/2000 | Crooke | |
| 7,196,184 B2 | 3/2007 | Heidenreich et al. | |
| 2003/0130186 A1 | 7/2003 | Vargeese et al. | |
| 2003/0143732 A1 | 7/2003 | Fosnaugh et al. | |
| 2003/0190654 A1 | 10/2003 | Heidenreich et al. | |
| 2004/0259247 A1 | 12/2004 | Tuschl et al. | |
| 2005/0107325 A1 | 5/2005 | Manoharan et al. | |
| 2005/0159381 A1 | 7/2005 | McSwiggen et al. | |
| 2007/0004664 A1 | 1/2007 | McSwiggen et al. | |
| 2007/0031844 A1 | 2/2007 | Khvorova et al. | |

FOREIGN PATENT DOCUMENTS

| | | |
|---|---|---|
| WO | WO 2003/062432 A1 | 7/2003 |
| WO | WO 2003/070972 A2 | 8/2003 |
| WO | WO 2004/064737 | 8/2004 |
| WO | WO 2004/080406 | 9/2004 |
| WO | WO 2004/094345 | 11/2004 |
| WO | WO 2005/115481 | 12/2005 |

OTHER PUBLICATIONS

Bertrand et al. (Biochemical and Biophysical Research Communications, 2002, 296, pp. 1000-1004).*
Elbashir et al. (The EMBO Journal, vol. 20, No. 23, pp. 6877-6888, 2001).*
European Search Report for European Patent Application No. EP 09007997.1, Nov. 2, 2009, 6 pages.
Supplementary European Search Report for European Patent Application No. EP 05857009.4, Mar. 23, 2009, 8 pages.
Wohlbold, L., et al., "Repeated application of sequence-specific siRNA molecules leads to an effective downmodulation of all clinically relevant bcr-abl gene variants," Blood, Nov. 2004, p. 165B, Part 2, vol. 104, No. 11 (Abstract).
Smetsers, T., et al., "An antisense Bcr-Abl phosphodiester-tailed methylphosphonate oligonucleotide reduces the growth of chronic myeloid leukaemia patient cells by a non-antisense mechanism" British Journal of Haematology, 1997, vol. 96, No. 2, 1997, pp. 377-381.
Boese, et al. "Mechanistic Insights Aid Computational Short Interfering RNA Design," Methods in Enzymology 392:73-96, 2005.
Reynolds, et al. "Rational RNA Design for RNA Interference," Nature Biotechnology 22:326-330, 2004.
Barnes et al., "Cytogenetic and Molecular Genetic Aspects of Chronic Myeloid Leukaemia" Acta Haematologica 108:180-202 (2002).
Byrom, W.M., et al., "Inducing RNAi with siRNA Cocktails Generated by RNase III" Tech Notes 10 (1), Ambion, Inc., Austin, TX, USA, Mar. (2003).
Castelli et al., A Study of the Interferon Antiviral Mechanism: Apoptosis Activation by the 2-5A System: J. Exp. Med. 186(6):967-972 (1997).
Chen et al., "Stable expression of small interfering RNA sensitizes TEL-PDGF(3R to inhibition with imatinib or rapamycin" J. Clin Invest. 113(12):1784-1791 (2004).
Chen et al., "Gene therapy for brain tumors: regression of experimental gliomas by adenovirus-mediated gene transfer in vivo" Proc. Nat!. Acad. Sci. USA 91:3054-3057 (1994).
Corbin et al., "Analysis of the structural basis of specificity of the Abl kinase by STI571" J. Biol. Chem. 277:32214-32219 (2001).
Damm-Welk, C., et al., "Targeting oncogenic fusion genes in leukemias and lymphomas by RNA interference," Semin Cancer Biol., 2003, pp. 283-292, vol. 13.
Dohjima, T., et al., "Small interfering RNAs expressed from a Pol III promoter suppress the EWS/FLI-1 transcript in an Ewing sarcoma cell line," Mol. Ther., 2003, pp. 811-816, vol. 7.
Elbashir et al., "RNA interference is mediated by 21- and 22-nucleotide RNAs" Genes and Dev. 15:188-200 (2001).
Faderl et al., "The Biology and Therapy of Adult Acute Lymphoblastic Leukemia" Cancer (7):1337-1354 (2003).
Fire et al "Potent specific genetic interference by double stranded RNA in *Caenorhabditis elegans*" Nature 391:806-811 (1998).
Goetz et al., "Requirement for Mdm2 in the Survival Effects of Bcr-Abl and Interleukin 3 in Hematopoietic Cells" Cancer Res. 61:7635-7641 (2001).
Heidel, et al., "Lack of interferon response in animals to naked siRNAs" Nature Biotechn 22 (12):1579-1582 (2004).

(Continued)

*Primary Examiner* — Amy Bowman
(74) *Attorney, Agent, or Firm* — Fenwick & West LLP

(57) ABSTRACT

The invention relates to compositions and methods for modulating the expression of Bcr-Abl, and more particularly to the down-regulation of Bcr-Abl mRNA and Bcr-Abl protein levels by oligonucleotides via RNA interference, e.g., chemically modified oligonucleotides.

15 Claims, 4 Drawing Sheets

OTHER PUBLICATIONS

Heidenreich et al., "AML1/MTG8 oncogene suppression by small interfering RNAs supports myeloid differentiation of t(8;21)-positive leukemic cells" Blood 101(8):3157-3163 (2003).

Heisterkamp et al., "Localization of the c-abl oncogene adjacent to a translocation break point in chronic m eloc 'c leukaemia" Nature 306:239-242 1983.

Khvorova, A., et al., "Functional siRNAs and miRNAs exhibit stand bias," Cell, 2003, pp. 209-216, vol. 115.

Kronenwett R, et al., Kinetic selectivity of complementary nucleic acids: bcr-abl-directed antisense RNA and ribozymes. J Mol Biol. 1996; 259: 632-644.

Kurzrock et al., "Philadelphia Chromosome-Positive Leukemias: From Basic Mechanisms to Molecular Thera eutics" Ann. Intern. Med. 138:819-831 (2003).

Lee et al., "The Interferon-Induced Double-Stranded RNA-Activated Protein Kinase Induces Apoptosis" Virology 199:491-496 (1994).

Li et al., "Specific Killing of Ph Chronic Myeloid Leukemia Cells by a Lentiviral Vector-Delivered Anti-bcr/abl Small Hairpin RNA" Oligonucleotides 13:401-409 (2003).

Limbach et al., "Summary: the modified nucleosides of RNA" Nucleic Acids Res. 22:2183-2196 (1994).

Manche et al., "Interactions between Double-Stranded RNA Regulators and the Protein Kinase DAP" Mol. Cell. Biol. 12(11):5238-5248 (1992).

Mittal, "Improving the Efficiency of RNA Interference in Mammals" Nat. Rev. Genet.5:355-365 (2004).

Novina, C., et al., "The RNAi revolution," Nature, Jul. 8, 2004, pp. 161-164, vol. 430.

Nowell, P.C., et al., "Radiation Environment in Space" Science 132(3438):1465-1472 (1960).

Nowell, P.C., et al., "A minute chromosome in human chronic granulocytic leukemia," Science, Nov. 18, 1960, p. 1467, vol. 132, No. 3438.

Nykanen et al., "ATP requirements and small interfering RNA structure in the RNA interference pathway" Cell 107:309-321 (2001).

Ritter et al., "Design and Evaluation of Chemically Synthesized siRNA Targeting the NPM-ALK Fusion Site in Ana plastic Large Cell Lymphoma (ALCL)" Oligonucleotides 13:365-373 (2003).

Rothberg, "Imatinib: resisting the resistance" Leukemia Res. 27:977-978 (2003).

Rowley, "A New Consistent Chromosomal Abnormality in Chronic Myelogenous Leukaemia identified by Quinacrine Fluorescence and Giemsa Staining" Nature 243:290-293 (1973).

Scherr et al., "Specific Inhibition of bcr-abl gene expression by small interfering RNA" Blood 101 4:1566-1569 (2003).

Schwarz, D.S., et al., "Asymmetry in the assembly of the RNAi Enzyme complex," Cell, 2003, pp. 199-208, vol. 115.

Song, E., et al., "RNA interference targeting Fas protects mice from fulminate hepatitis," Nature Medicine, 2003, pp. 347-351, vol. 9.

Spiller et al., "The Influence of Target Protein Half-Life on the Effectiveness of Antisense Oligonucleotide Analog-Mediated Biologic Responses" Antisense Nucleic Acid Drug Dev. 8:281-293-1998.

Van der Kuip et al., "Adhesion to fibronectin selectively protects Bcr-Abl+ cells from DNA damage-induced apoptosis" Blood 98:1532-1541, 2001.

Westbrook et al., "Clinical Significance of the BCR-ABL Fusion Gene in Adult Acute Lymphoblastic Leukemia: A Cancer and Leukemia Group B Study (8762)" Blood 80:2983-2990 (1992).

Wilda et al., "Killing of leukemic cells with a BCR/ABL fusion gene by RNA interference (RNAi)" Oncogene 21:5716-5724 (2002).

Wohlbold et al., "Inhibition of bcr-abl gene expression by small interfering RNA sensitizes for imatinib mesylate (ST1571)" Blood 102(6):2236-2239 (2003).

Wilson, J.A., et al., "Induction of RNA interference using short interfering RNA expression vectors in cell culture and animal systems," Current Opinion in Molecular Therapeutics, 2003, pp. 389-396, vol. 5, No. 4.

Yang et al., "Short RNA duplexes produced by hydrolysis with *Escherichia coli* RNase III mediate effective RNA interference in mammalian cells" PNAS 99:9942-9947 (2002).

Zheng et al., "Activation of the protein kinase PKR by short double-stranded RNAs with single-'stranded tails" RNA 10:1934-1945 2004.

Vickers et al., "Efficient Reduction of target RNAs by Small Interfering RNA and RNase H-dependent Antisense Agents," Journal of Biological Chemistry 278(9):7108-7118 (2002).

Agrawal, S., et al., "Antisense oligonucleotides: towards clinical trials." Trends in Biotechnology. Oct. 1996, vol. 14, pp. 376-387.

Bass, B., "The short answer," Nature, May 24, 2001, pp. 428-429, vol. 411.

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "Functional Anatomy of siRNAs for Mediating Efficient RNAi in *Drosophila Melanogaster* Embryo Lysate", The EMBO Journal, 2001, pp. 6877-6888, vol. 20, No. 23.

Fire, A., "RNA-triggered Gene Silencing," Trends in Genetics, Sep. 1999, pp. 358-363, vol. 15, No. 9.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA In Vitro," Genes & Development, 1999, pp. 3191-3197, vol. 13.

Tuschl, T., "Expanding small RNA interference," Nature Biotechnology, May 2002, pp. 446-448, vol. 20.

* cited by examiner ural Application No. 60/630,878, filed on Nov. 24, 2004,

SEQUENCE LISTING

<160> NUMBER OF SEQ ID NOS: 30

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 1
cagaguucaa aagcccuuca g                                              21

<210> SEQ ID NO 2
<211> LENGTH: 23

```
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 2
ucgucucaag uuuucgggaa guc                                               23

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 3
caguguucau aagccguuca g                                                 21

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 4
cugaacggcu uaugaacacu gcu                                               23

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 5
agaguucaaa agcccuucag c                                                 21

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 6
cgucucaagu uuucgggaag ucg                                               23

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 7
cagaguugaa aagcccuuca g                                                 21

<210> SEQ ID NO 8
<211> LENGTH: 23
<212> TYPE: RNA
<213> ORGANISM: Artificial Sequence
```

```
<220> FEATURE:
<223> OTHER INFORMATION: Description of Artificial Sequence:
      Synthetically generated iRNA

<400> SEQUENCE: 8
cugaagggcu uucaacucu gcu                                              23

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 9
uaaggaagaa gcccuucagc g                                               21

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 10
cgcugaaggg cuucuuccuu auu                                             23

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 11
aauaaggaag aagcccuuca g                                               21

<210> SEQ ID NO 12
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 12
aguuauuccu ucuucgggaa guc                                             23

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 13
ggaagaagcc cuucagcggc c                                               21

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence:
```

-continued

Synthetically generated iRNA

<400> SEQUENCE: 14
uuccuucuuc gggaagucgc cgg                    23

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 15
aucaauaagg aagaagcccu u                      21

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 16
gguaguuauu ccuucuucgg gaa                    23

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 17
aucuauaagc aagaaccccu u                      21

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 18
aagggguucu ugcuuauaga ugg                    23

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 19
ggagacgcag aagcccuuca g                      21

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

```
<400> SEQUENCE: 20
uaccucugcg ucuucgggaa guc                                    23

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 21
gacgcagaag cccuucagcg g                                      21

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 22
ccgcugaagg gcuucugcgu cuc                                    23

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 23
cugaagggcu uuugaacucu gcu                                    23

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 24
gcugaagggc uuuugaacuc ugc                                    23

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 25
cugaagggcu ucuuccuuau uga                                    23

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 26
```

```
ggccgcugaa gggcuucuuc cuu                                              23

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 27
aagggcuucu uccuuauuga ugg                                              23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence:
      Synthetically generated iRNA

<400> SEQUENCE: 28
cugaagggcu ucugcgucuc cau                                              23

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 29
ctgacatccg tggagctg                                                    18

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 30
cattgtgatt atagcctaag a                                                21
```

RNAI MODULATION OF THE BCR-ABL FUSION GENE AND USES THEREOF

CROSS-REFERENCE TO RELATED APPLICATIONS

This application is a divisional of U.S. application Ser. No. 12/171,291 (abandoned), filed Jul. 10, 2008, which is a continuation of U.S. application Ser. No. 11/286,624, filed Nov. 23, 2005 (abandoned) which claims priority to U.S. Provisional Application No. 60/630,878, filed on Nov. 24, 2004, and to U.S. Provisional Application No. 60/632,403, filed on Dec. 1, 2004. The entire contents of these applications are hereby incorporated by reference in the present application.

REFERENCE TO A SEQUENCE LISTING

The instant application contains a Sequence Listing which has been submitted via EFS-Web and is hereby incorporated by reference in its entirety. Said ASCII copy, created on May 18, 2010, is named 15604US_CRF_sequencelisting.txt and is 7,592 bytes in size.

TECHNICAL FIELD

The invention relates to compositions and methods for modulating the expression of Bcr-Abl, and more particularly to the down-regulation of Bcr-Abl mRNA and Bcr-Abl protein levels by oligonucleotides via RNA interference, e.g., chemically modified oligonucleotides.

BACKGROUND

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function.

The discovery of the Philadelphia Chromosome (Ph) represented the first consistent chromosomal abnormality causing a specific human cancer (Nowell P C et al., 1960, Science 132:1467). The Ph Chromosome is generated by a reciprocal translocation between the long arms of Chromosome 9 and Chromosome 22 (Rowley J D, 1973, Nature, 243:290-293.). It occurs in almost all patients with chronic myelogenous leukemia (CML), in about 10-20% of the adults with acute lymphoblastic leukemia (ALL) (Westbrook C A et al., 1992 Blood, 80:2983) and about 2% of patients with acute myelogenous leukemia (AML). The t(9;22) translocation fuses the Bcr gene from Chromosome 22 and the Abl gene from chromosome 9, resulting in the oncogenic Bcr-Abl fusion-gene (Heisterkamp N et al., 1983, Nature, 306:239). Variable breakpoints within the Bcr gene on chromosome 22 lead to the formation of different Bcr-Abl fusion gene variants which encode for different proteins p190$^{Bcr-Abl}$ (Mr 190,000), p210$^{Bcr-Abl}$ (Mr 210,000) and p230$^{Bcr-Abl}$ (Mr 230,000). In about 95% of the CML-patients the Bcr-Abl fusion transcripts e14a2 (former b3a2) and e13a2 (former b2a2) can be detected (reviewed in Barnes et al., 2002, Acta Haematologica, 108:180-202). The translated product is in each case a p210 kD Bcr-Abl protein. In patients with Ph+ALL a shorter transcript version called Bcr-Abl-e1a2, predominates (reviewed in Faderl et al., 2003, Cancer, 98:1337). Translation of this variant results in the somewhat lighter p190$^{Bcr-Abl}$ protein. Both Bcr-Abl proteins p190$^{Bcr-Abl}$ and p210$^{Bcr-Abl}$ are characterised by a dramatically increased tyrosine-kinase activity, as compared to that of normal Abl protein, leading to aberrant phosphorylation of downstream target molecules.

The kinase activity of Bcr-Abl can be inhibited by a specific tyrosine kinase inhibitor, Imatinib mesylate (STI571, Glivec), which is effective for treatment of Ph+leukemia (reviewed in Kurzrock et al., 2003, Ann. Intern. Med., 138:819). Nevertheless, both ALL and advanced CML patients frequently develop drug resistance after initial response predominantly caused by genetic abnormalities such as point mutations in the Bcr-Abl kinase domain or overexpression of Bcr-Abl (for review: Rothberg, 2003, Leukemia Res., 27:977). Therefore the development of alternative strategies to inhibit Bcr-Abl becomes increasingly important.

The breakpoint of the Bcr-Abl mRNA represents a unique and leukemia-specific nucleotide sequence. Such fusion transcripts encoding oncogenic proteins represent ideal targets for a disease-specific RNAi approach. The possibility to use RNAi for the specific degradation of the Bcr-Abl-e14a2 transcript variant, as well as other oncogenic fusion proteins, has been demonstrated recently (Wilda et al., Oncogene 2002, 21:5716; Scherr et al., Blood 2003, 101:1566; Heidenreich et al., Blood. 2003, 101:3157, Wohlbold et al., Blood 2003, 102:2236; Ritter U, et al., Oligonucleotides 2003, 13:365; Li et al., Oligonucleotides 2003, 13:401; Chen J, et al., J Clin Invest. 2004, 113:1784). The results presented are inconclusive, as Wilda et al. did not observe a sensitizing effect towards imatinib mesylate on Bcr-Abl-expressing cells by treatment with Bcr-Abl-specific siRNAs, whereas others did observe such effects. It was therefore unclear so far, whether the expression of two relevant Bcr-Abl transcripts other than the e14a2 transcript variant (e13a2 and e1a2) can be down-regulated by an RNAi approach.

The present invention advances the art by providing methods and medicaments encompassing short dsRNAs leading to the down-regulation of p210$^{Bcr-Abl}$ and p190$^{Bcr-Abl}$ protein levels in murine 32D cells expressing the respective Bcr-Abl gene variants, in human leukemic MEG-01, K562 and SUP-B15 cells, and in cells freshly isolated from human subjects suffering from leukemia. These methods and medicaments may be used in research into, and in the treatment of, certain cancers.

SUMMARY

The present invention is based on an investigation of the Bcr-Abl fusion gene using iRNA agents and further testing of the iRNA agents that target the fusion sites of Bcr-Abl breakpoint variants. Based on these findings, the present invention provides compositions and methods that are useful in reducing Bcr-Abl mRNA levels, Bcr-Abl fusion protein levels and undesirable cell proliferation in a subject, e.g., a mammal, such as a human.

The present invention specifically provides iRNA agents consisting of or comprising at least 15 contiguous nucleotides of one of the agents described in Table 1, agent numbers 1-6. The iRNA agent preferably comprises less than 30 nucleotides per strand, e.g., 21-23 nucleotides. The double stranded iRNA agent can either have blunt ends or more preferably have overhangs of 1-4 nucleotides from one or both 3' ends of the agent.

Further, the iRNA agent can either contain only naturally occurring ribonucleotide subunits, or can be synthesized so as to contain one or more modifications to the sugar or base of one or more of the ribonucleotide subunits that is included in the agent. The iRNA agent can be further modified so at to be attached to a ligand that is selected to improve stability, distribution or cellular uptake of the agent, e.g. cholesterol. The agents can further be in isolated form or can be part of a pharmaceutical composition used for the methods described herein.

The present invention further provides methods for reducing the level of Bcr-Abl fusion mRNA in a cell. The present methods utilize the cellular mechanisms involved in RNA interference to selectively degrade Bcr-Abl fusion mRNA in a cell and are comprised of the step of contacting a cell with one of the iRNA agents of the present invention. Such methods can be performed directly on a cell or can be performed on a mammalian subject by administering to a subject one of the iRNA agents of the present invention. Reduction of Bcr-Abl fusion mRNA in a cell results in a reduction in the amount of Bcr-Abl fusion protein produced, and in an organism, may result in a decrease in undesirable cell proliferation, or it may sensitize proliferating cells towards the activity of another agent, e.g. a cytostatic or cytotoxic agent, e.g. imatinib mesylate or gamma radiation.

The methods and compositions of the invention, e.g., the methods and iRNA compositions can be used with any dosage and/or formulation described herein, as well as with any route of administration described herein.

The details of one or more embodiments of the invention are set forth in the accompanying drawings and the description below. Other features, objects, and advantages of the invention will be apparent from this description, the drawings, and from the claims. This application incorporates all cited references, patents, and patent applications by references in their entirety for all purposes.

BRIEF DESCRIPTION OF DRAWINGS

FIG. 1A: Western blot analysis of p210$^{Bcr-abl}$ (e13a2) in 32Dp210/e13a2~24 h following siRNA treatment; the level of GAPDH served as loading control. Lane 1: EPC, Lane 2: BAF9, Lane 3: BAF3, Lane 4: BAF15, Lane 5: BAF17, Lane 6: BAF19. FIG. 1B: Prolonged treatment with the siRNAs BAF15 as well as BAF19 led to a reduction of viability in 32Dp210/e13a2 cells. ~40 h following the indicated number of siRNA treatments, viability of cells was determined by means of MTT. Values are means +/− SD of triplicates.

FIG. 2A: Western blot analysis of p190$^{Bcr-abl}$ (e1a2) in 32Dp190/e1a2 cells about 24 h following second siRNA treatment; the level of GAPDH served as loading control. Lane 1: EPC, Lane 2: BAF9, Lane 3: BAF19, Lane 4: BAF22, Lane 5: BAF24. FIG. 2B: repeated treatment with the siRNA BAF22 led to a reduction of viability in 32Dp190/e1a2 cells. ~40 h following the second siRNA treatment, viability of cells was determined by means of MTT. Values are means +/− SD of triplicates.

DETAILED DESCRIPTION

Figure 1A:
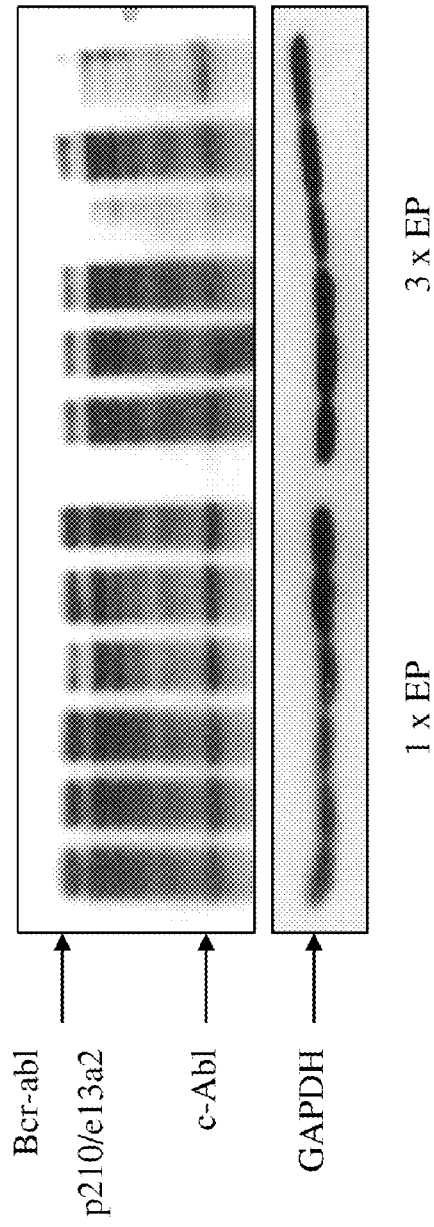
FIGS. 1A-1B: ~2.5 Mio 32Dp210/e13a2 cells have been electroporated 1-3×at intervals of 24 h with the indicated siRNA. BAF3/BAF15/BAF17/BAF19: bcr-abl-e13a2-specific siRNAs; BAF9: bcr-abl-e14a2-specific siRNA, served as control; EPC: electroporation control.
Figure 1B:
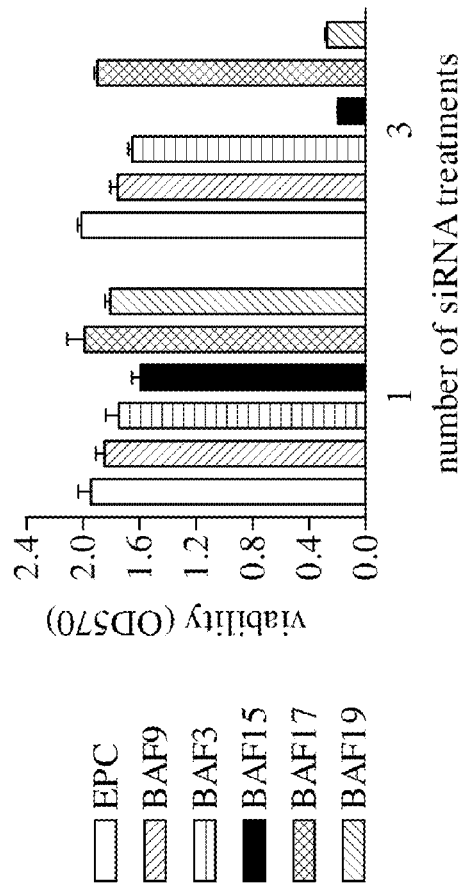

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogates, all of which are described herein or are well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can downregulate the expression of a target gene, e.g., a Bcr-Abl fusion gene. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded iRNA agent.

A "ds iRNA agent" (abbreviation for "double stranded iRNA agent"), as used herein, is an iRNA agent which includes more than one, and preferably two, strands in which interstrand hybridization can form a region of duplex structure. A "strand" herein refers to a contiguous sequence of nucleotides (including non-naturally occurring or modified nucleotides). The two or more strands may be, or each form a part of, separate molecules, or they may be covalently interconnected, e.g. by a linker, e.g. a polyethyleneglycol linker, to form but one molecule. At least one strand can include a region which is sufficiently complementary to a target RNA. Such strand is termed the "antisense strand". A second strand comprised in the dsRNA agent which comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand"

refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host (Manche, L., et al., Mol. Cell. Biol. 1992, 12:5238; Lee. SB, Esteban, M, Virology 1994, 199:491; Castelli, J C, et al., J. Exp. Med. 1997, 186:967; Zheng, X., Bevilacqua, P C, RNA 2004, 10:1934; Heidel et al., "Lack of interferon response in animals to naked siRNAs", Nature Biotechn. advance online publication, Nov. 21, 2004, doi: 10.1038/nbt1038). The iRNA agents of the present invention include molecules which are sufficiently short that they do not trigger a deleterious non-specific interferon response in normal mammalian cells. Thus, the administration of a composition of an iRNA agent (e.g., formulated as described herein) to a subject can be used to silence expression of the Bcr-Abl fusion gene in Bcr-Abl expressing cells comprised in the subject, while circumventing an interferon response, especially in other cells not expressing Bcr-Abl. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 60 but preferably less than 50, 40, or 30 nucleotide pairs.

The isolated iRNA agents described herein, including ds iRNA agents and siRNA agents, can mediate silencing of an Bcr-Abl fusion gene, e.g., by RNA degradation. For convenience, such RNA is also referred to herein as the RNA to be silenced. Such a gene is also referred to as a target gene. Preferably, the RNA to be silenced is a gene product of an endogenous Bcr-Abl fusion gene.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

As used herein, the term "complementary" is used to indicate a sufficient degree of complementarity such that stable and specific binding occurs between a compound of the invention and a target RNA molecule, e.g. an Bcr-Abl fusion mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target Bcr-Abl fusion mRNA) if the iRNA agent reduces the production of a protein encoded by the target RNA in a cell. The iRNA agent may also be "exactly complementary" to the target RNA, e.g., the target RNA and the iRNA agent anneal, preferably to form a hybrid made exclusively of Watson-Crick basepairs in the region of exact complementarity. A "sufficiently complementary" iRNA agent can include an internal region (e.g., of at least 10 nucleotides) that is exactly complementary to a target Bcr-Abl fusion RNA. Moreover, in some embodiments, the iRNA agent specifically discriminates a single-nucleotide difference. In this case, the iRNA agent only mediates RNAi if exact complementarity is found in the region (e.g., within 7 nucleotides of) the single-nucleotide difference. Preferred iRNA agents will be based on or consist or comprise the sense and antisense sequences provided in Table 1, agent numbers 1-6.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil). "Essentially retaining the ability to inhibit Bcr-Abl fusion expression in cultured human Bcr-Abl expressing cells", as used herein referring to an iRNA agent not identical to but derived from one of the iRNA agents of Table 1, agent numbers 1-6, by deletion, addition or substitution of nucleotides, means that the derived iRNA agent possesses an inhibitory activity lower by not more than 20% inhibition compared to the iRNA agent of Table 1, agent numbers 1-6, it was derived from. E.g. an iRNA agent derived from an iRNA agent of Table 1, agent numbers 1-6, which lowers the amount of Bcr-Abl fusion mRNA present in cultured human Bcr-Abl expressing cells by 70% may itself lower the amount of Bcr-Abl fusion mRNA present in cultured human Bcr-Abl expressing cells by at least 50% in order to be considered as essentially retaining the ability to inhibit Bcr-Abl fusion expression in cultured human Bcr-Abl expressing cells. Optionally, an iRNA agent of the invention may lower the amount of Bcr-Abl fusion mRNA present in cultured human Bcr-Abl expressing cells by at least 50%.

As used herein, a "subject" refers to a mammalian organism undergoing treatment for a disorder mediated by Bcr-Abl fusion protein expression. The subject can be any mammal, such as a cow, horse, mouse, rat, dog, pig, goat, or a primate. In the preferred embodiment, the subject is a human.

As used herein, disorders associated with Bcr-Abl fusion expression refers to any biological or pathological state that 1) is mediated in part by the presence of Bcr-Abl fusion protein and 2) whose outcome can be affected by reducing the level of Bcr-Abl fusion protein present. Specific disorder associated with Bcr-Abl fusion expression are noted below.

1 Design and Selection of iRNA Agents

TABLE 1

Exemplary iRNA agents to target Bcr-Abl fusion mRNA

| SEQ. ID No. | Sequence sense strand[a,b] | SEQ. ID No. | Sequence antisense strand[a,b] | Duplex descriptor | Specific for Bcr-Abl fusion gene variant | Agent number |
|---|---|---|---|---|---|---|
| 1 | cagaguucaa\|aagcccuucag | 23 | cugaagggcuu\|uugaacucugcu | BAF7 | Bcr-Abl-e14a2 | 1 |
| 5 | agaguucaa\|aagcccuucagc | 24 | gcugaagggcuu\|uugaacucugc | BAF9 | Bcr-Abl-e14a2 | 2 |

TABLE 1-continued

Exemplary iRNA agents to target Bcr-Abl fusion mRNA

| SEQ. ID No. | Sequence sense strand[a,b] | SEQ. ID No. | Sequence antisense strand[a,b] | Duplex descriptor | Specific for Bcr-Abl fusion gene variant | Agent number |
|---|---|---|---|---|---|---|
| 11 | aauaaggaag\|aagcccuucag | 25 | cugaagggcuu\|cuuccuuauuga | BAF15 | Bcr-Abl-e13a2 | 3 |
| 13 | *g*gaag\|aagcccuucagcggcc | 26 | *g*gccgcugaagggcuu\|cuuccuu | BAF17 | Bcr-Abl-e13a2 | 4 |
| 15 | aucaauaaggaag\|aagcccuu | 27 | aagggcuu\|cuuccuuauugaugg | BAF19 | Bcr-Abl-e13a2 | 5 |
| 19 | *g*gagacgcag\|aagcccuucag | 28 | cugaagggcuu\|cugcgucuccau | BAF22 | Bcr-Abl-e1a2 | 6 |

[a]See Table 2 for an explanation of nucleotide representation (e.g., lower case letters bold and italicized letters).
[b]exact Bcr-Abl fusion site is marked by hyphen;

The present invention is based on the demonstration of silencing of an Bcr-Abl fusion gene in vitro in cultured cells after incubation with an iRNA agent, and the resulting reduction in cell proliferation.

An iRNA agent can be rationally designed based on sequence information and desired characteristics. For example, an iRNA agent can be designed according to the relative melting temperature of the candidate duplex. Generally, the duplex should have a lower melting temperature at the 5' end of the antisense strand than at the 3' end of the antisense strand.

Candidate iRNA agents can also be designed by performing, for example, a gene walk analysis of the genes that will serve as the target gene. Overlapping, adjacent, or closely spaced candidate agents corresponding to all or some of the transcribed region can be generated and tested. Each of the iRNA agents can be tested and evaluated for the ability to down regulate the target gene expression (see below, "Evaluation of Candidate iRNA agents").

Herein, potential iRNA agents targeting the Bcr-Abl fusion variants Bcr-Abl-e14a2, Bcr-Abl-e13a2, and Bcr-Abl-e1a2 were designed using the known sequences of the respective fusion sites (Barnes et al., 2002, Acta Haematologica, 108:180-202; Faderl et al., 2003, Cancer, 98:1337). Based on the results provided, the present invention provides iRNA agents that silence these Bcr-Abl fusion gene breakpoint variants.

Table 1 provides active iRNA agents targeting Bcr-Abl fusion, specifically agent numbers 1-6. As shown in the Examples below, the iRNA agents of Table 1, agent numbers 1-6, possess the advantageous and surprising ability to reduce the amount of Bcr-Abl fusion mRNA present in cultured human Bcr-Abl expressing cells after incubation with these agents by more than 50% (and with some agents, more than 80%) compared to cells which have not been incubated with the agent, and/or to reduce the amount of Bcr-Abl fusion protein secreted into cell culture supernatant by cultured human Bcr-Abl expressing cells by more than 50%.

Based on these results, the invention specifically provides an iRNA agent that includes a sense strand having at least 15 contiguous nucleotides of the sense strand sequences of the agents provided in Table 1, agent numbers 1-6, and an antisense strand having at least 15 contiguous nucleotides of the antisense sequences of the agents provided in Table 1, agent numbers 1-6.

The iRNA agents shown in Table 1 are composed of a sense strand of 21 nucleotides in length, and an antisense strand of 23 nucleotides in length and the present invention provides agents that comprise 15 contiguous nucleotides from these agents. However, while these lengths may potentially be optimal, the iRNA agents are not meant to be limited to these lengths. The skilled person is well aware that shorter or longer iRNA agents may be similarly effective, since, within certain length ranges, the efficacy is rather a function of the nucleotide sequence than strand length. For example, Yang, D., et al., PNAS 2002, 99:9942-9947, demonstrated similar efficacies for iRNA agents of lengths between 21 and 30 base pairs. Others have shown effective silencing of genes by iRNA agents down to a length of approx. 15 base pairs (Byrom, W. M., et al., Inducing RNAi with siRNA Cocktails Generated by RNase III; Tech Notes 10(1), Ambion, Inc., Austin, Tex., USA).

Therefore, it is possible and contemplated by the instant invention to select from the sequences provided in Table 1, agent numbers 1-6, a partial sequence of between 15 to 22 nucleotides for the generation of an iRNA agent derived from one of the sequences provided in Table 1, agent numbers 1-6. Alternatively, one may add one or several nucleotides to one of the sequences provided in Table 1, agent numbers 1-6, or an agent comprising 15 contiguous nucleotides from one of these agents, preferably, but not necessarily, in such a fashion that the added nucleotides are complementary to the respective sequence of the target gene, e.g. Bcr-Abl fusion. For example, the first 15 nucleotides from one of the agents can be combined with the 8 nucleotides found 5' to these sequence in the Bcr-Abl fusion mRNA to obtain an agent with 23 nucleotides in the sense and antisense strands. All such derived iRNA agents are included in the iRNA agents of the present invention, provided they essentially retain the ability to inhibit Bcr-Abl fusion expression in cultured human Bcr-Abl expressing cells.

The antisense strand of an iRNA agent should be equal to or at least, 14, 15, 16 17, 18, 19, 25, 29, 40, or 50 nucleotides in length. It should be equal to or less than 60, 50, 40, or 30, nucleotides in length. Preferred ranges are 15-30, 17 to 25, 19 to 23, and 19 to 21 nucleotides in length.

The sense strand of an iRNA agent should be equal to or at least 14, 15, 16 17, 18, 19, 25, 29, 40, or 50 nucleotides in length. It should be equal to or less than 60, 50, 40, or 30 nucleotides in length. Preferred ranges are 15-30, 17 to 25, 19 to 23, and 19 to 21 nucleotides in length.

The double stranded portion of an iRNA agent should be equal to or at least, 15, 16 17, 18, 19, 20, 21, 22, 23, 24, 25, 29, 40, or 50 nucleotide pairs in length. It should be equal to or less than 60, 50, 40, or 30 nucleotides pairs in length. Preferred ranges are 15-30, 17 to 25, 19 to 23, and 19 to 21 nucleotides pairs in length.

Generally, the mRNA agents of the instant invention include a region of sufficient complementarity to the respective Bcr-Abl fusion gene, and are of sufficient length in terms of nucleotides, that the iRNA agent, or a fragment thereof, can mediate down regulation of the Bcr-Abl fusion gene. The antisense strands of the iRNA agents of Table 1, agent numbers 1-6, are fully complementary to the mRNA sequences of the respective Bcr-Abl fusion gene, and their sense strands are fully complementary to the antisense strands except for the two 3'-terminal nucleotides on the antisense strand. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an Bcr-Abl fusion mRNA.

Therefore, the iRNA agents of the instant invention include agents comprising a sense strand and antisense strand each comprising a sequence of at least 16, 17 or 18 nucleotides which is essentially identical, as defined below, to one of the sequences of Table 1, agent numbers 1-6, except that not more than 1, 2 or 3 nucleotides per strand, respectively, have been substituted by other nucleotides (e.g. adenosine replaced by uracil), while essentially retaining the ability to inhibit Bcr-Abl expression in cultured human Bcr-Abl expressing cells. These agents will therefore possess at least 15 nucleotides identical to one of the sequences of Table 1, agent numbers 1-6, but 1, 2 or 3 base mismatches with respect to either the target Bcr-Abl fusion mRNA sequence or between the sense and antisense strand are introduced. Mismatches to the target Bcr-Abl fusion mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length, at one or both ends of the iRNA agent. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the siRNA agent range discussed above. siRNA agents can resemble in length and structure the natural Dicer processed products from long dsRNAs. Embodiments in which the two strands of the siRNA agent are linked, e.g., covalently linked, are also included. Hairpin, or other single strand structures which provide the required double stranded region, and preferably a 3' overhang are also within the invention.

2 Evaluation of Candidate iRNA Agents

A candidate iRNA agent can be evaluated for its ability to downregulate target gene expression. For example, a candidate iRNA agent can be provided, and contacted with a cell, that expresses the target gene, e.g., the Bcr-Abl fusion gene, either endogenously or because it has been transfected with a construct from which a Bcr-Abl fusion protein can be expressed. The level of target gene expression prior to and following contact with the candidate iRNA agent can be compared, e.g. on an mRNA or protein level. If it is determined that the amount of RNA or protein expressed from the target gene is lower following contact with the iRNA agent, then it can be concluded that the iRNA agent downregulates target gene expression. The level of target Bcr-Abl fusion RNA or Bcr-Abl fusion protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis or immunofluorescence.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability.

In Vivo Testing

An iRNA agent identified as being capable of inhibiting Bcr-Abl fusion gene expression can be tested for functionality in vivo in an animal model (e.g., in a mammal, such as in mouse or rat). For example, the iRNA agent can be administered to an animal, and the iRNA agent evaluated with respect to its biodistribution, stability, and its ability to inhibit a Bcr-Abl fusion gene expression or reduce undesirable cell proliferation.

The iRNA agent can be administered directly to the target tissue, such as by injection, or the iRNA agent can be administered to the animal model in the same manner that it would be administered to a human.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}$S, $^{32}$P, $^{33}$P, or $^{3}$H; gold particles; or antigen particles for immunohistochemistry).

The iRNA agent can be evaluated with respect to its ability to down regulate Bcr-Abl fusion gene expression. Levels of Bcr-Abl fusion gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target Bcr-Abl fusion mRNA can be detected by any desired method, including but not limited to RT-PCR, Northern blot, branched-DNA assay, or RNAase protection assay. Alternatively, or additionally, Bcr-Abl fusion gene expression can be monitored by performing Western blot analysis on tissue extracts treated with the iRNA agent.

Animal models may be used to establish the concentration necessary to achieve a certain desired effect (e.g., EC50). Such animal models may include transgenic animals that express a human gene, e.g., a gene that produces a target human Bcr-Abl fusion RNA. In another embodiment, the composition for testing includes an iRNA agent that is complementary, at least in an internal region, to a sequence that is conserved between the target Bcr-Abl fusion RNA in the animal model and the target Bcr-Abl fusion RNA in a human.

3 iRNA Chemistry

Described herein are isolated iRNA agents, e.g., ds RNA agents that mediate RNAi to inhibit expression of an Bcr-Abl fusion gene.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because the are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Modifications described herein can be incorporated into any double-stranded RNA and RNA-like molecule described herein, e.g., an iRNA agent. It may be desirable to modify one or both of the antisense and sense strands of an mRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An mRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets Bcr-Abl fusion, can have enhanced resistance to nucleases.

One way to increase resistance is to identify cleavage sites and modify such sites to inhibit cleavage, as described in co-owned and co-pending applications U.S. Ser. No. 60/574, 744 and PCT/US2005/018931. For example, the dinucleotides 5'-ua-3', 5'-ca-3', 5'-ug-3', 5'-uu-3', or 5'-cc-3' can serve as cleavage sites. In certain embodiments, all the pyrimidines of an iRNA agent carry a 2'-modification in either the sense strand, the antisense strand, or both strands, and the iRNA agent therefore has enhanced resistance to endonucleases. Enhanced nuclease resistance can also be achieved by modifying the 5' nucleotide, resulting, for example, in at least one 5'-uridine-adenine-3' (5'-ua-3') dinucleotide wherein the uridine is a 2'-modified nucleotide; at least one 5'-cytidine-adenine-3' (5'-ca-3') dinucleotide, wherein the 5'-cytidine is a 2'-modified nucleotide; at least one 5'-uridine-guanine-3' (5'-ug-3') dinucleotide, wherein the 5'-uridine is a 2'-modified nucleotide; at least one 5'-uridine-uridine-3' (5'-uu-3') dinucleotide, wherein the 5'-uridine is a 2'-modified nucleotide; or at least one 5'-cytidine-cytidine-3' (5'-cc-3') dinucleotide, wherein the 5'-cytidine is a 2'-modified nucleotide, as described in co-owned International Application No. PCT/US2005/018931, filed on May 27, 2005. The iRNA agent can include at least 2, at least 3, at least 4 or at least 5 of such dinucleotides. In a particularly preferred embodiment, the 5' nucleotide in all occurrences of the sequence motifs 5'-ua-3' and 5'-ca-3' in either the sense strand, the antisense strand, or both strands is a modified nucleotide. Preferably, the 5' nucleotide in all occurrences of the sequence motifs 5'-ua-3',5'-ca-3' and 5'-ug-3' in either the sense strand, the antisense strand, or both strands is a modified nucleotide. More preferably, all pyrimidine nucleotides in the sense strand are modified nucleotides, and the 5' nucleotide in all occurrences of the sequence motifs 5'-ua-3' and 5'-ca-3' in the antisense strand are modified nucleotides, or where the antisense strand does comprise neither of a 5'-ua-3' and a 5'-ca-3' motif, in all occurrences of the sequence motif 5'-ug-3'.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-$OCH_3$, 2'-O -allyl, 2'-C— allyl, and 2'-fluoro.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An mRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include monomers which have been modified so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_P$) thioates. Thus, preferred NRMs include nucleotide dimers enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5'-end of an antisense sequence should have a terminal —OH or phosphate group this NRM is preferably not used at the 5'-end of an antisense sequence. The group should be attached at a position on the base which minimizes interference with H-bond formation and hybridization, e.g., away from the face which interacts with the complementary base on the other strand, e.g, at the 5' position of a pyrimidine or a 7-position of a purine;

(iii) nonphosphate linkages at the termini. Thus, preferred NRMs include non-phosphate linkages, e.g., a linkage of 4 atoms which confers greater resistance to cleavage than does a phosphate bond. Examples include 3' $CH_2$—$NCH_3$—O—$CH_2$-5' and 3' $CH_2$—NH—(O=)—$CH_2$-5';

(iv) 3'-bridging thiophosphates and 5'-bridging thiophosphates. Thus, preferred NRM's can include these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include, e.g., a targeting moiety or a conjugated ligand described herein conjugated with the monomer, e.g., through the sugar, base, or backbone. These are discussed in more detail below;

(vi) abasic linkages. Thus, preferred NRM's can include an abasic monomer, e.g., an abasic monomer (e.g., a nucleobaseless monomer); an aromatic or heterocyclic or polyheterocyclic aromatic monomer; and (vii) 5'-phosphonates and 5'-phosphate prodrugs. Thus, preferred NRM's include monomers, preferably at the terminal position, e.g., the 5' position, in which one or more atoms of the phosphate group is derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications can inhibit hybridization so it is preferable to use them only in terminal regions, and preferable to not use them at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the cleavage site, on the target or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sense or antisense strand.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP—$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease -resistance conferring moieties; and natural or unusual nucleobases. General examples include lipophilic moleculeses, lipids, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring substance or a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., an antibody that binds to a specified cell type such as a liver cell or a cell of the jejunum, a thyrotropin, melanotropin, lectin, glycoprotein, surfactant protein A, Mucin carbohydrate, glycosylated polyaminoacids, transferrin, bisphosphonate, polyglutamate, polyaspartate, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis -O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and protein or peptide conjugates (e.g., an antibody, a lipoprotein, e.g., low density lipoprotein, an albumin, e.g., human serum albumin(HSA)), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, folic acid), synthetic ribonucleases (e.g., imidazole, bisimidazole, histamine, imidazole clusters, acridine -imidazole conjugates, Eu3+ complexes of tetraazamacrocycles), dinitrophenyl, HRP, or AP.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins are the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

A targeting agent that incorporates a sugar, e.g., galactose and/or analogues thereof, is particularly useful. These agents target, in particular, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine, multivalent lactose, multivalent galactose, multivalent mannose, or multivalent fucose. A mannose or mannose-6-phosphate targeting moiety can be used for macrophage targeting.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Transport of iRNA Agents into Cells

Not wishing to be bound by any theory, the chemical similarity between cholesterol-conjugated iRNA agents and certain constituents of lipoproteins (e.g. cholesterol, cholesteryl esters, phospholipids) may lead to the association of iRNA agents with lipoproteins (e.g. LDL, HDL) in blood and/or the interaction of the iRNA agent with cellular components having an affinity for cholesterol, e.g. components of the cholesterol transport pathway. Lipoproteins as well as their constituents are taken up and processed by cells by various active and passive transport mechanisms, for example, without limitation, endocytosis of LDL-receptor bound LDL, endocytosis of oxidized or otherwise modified LDLs through interaction with Scavenger receptor A, Scavenger receptor B1-mediated uptake of HDL cholesterol in the liver, pinocytosis, or transport of cholesterol across membranes by ABC (ATP-binding cassette) transporter proteins, e.g. ABC-A1, ABC-G1 or ABC-G4. Hence, cholesterol-conjugated iRNA agents could enjoy facilitated uptake by cells possessing such transport mechanisms, e.g. cells of the liver. As such, the present invention provides evidence and general methods for targeting iRNA agents to cells expressing certain cell surface components, e.g. receptors, by conjugating a natural ligand for such component (e.g. cholesterol) to the iRNA agent, or by conjugating a chemical moiety (e.g. cholesterol) to the iRNA agent which associates with or binds to a natural ligand for the component (e.g. LDL, HDL).

4 Other Embodiments

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328, 470), or by stereotactic injection (see, e.g., Chen et al., *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into siRNA agent fragments that mediate gene silencing.

5 Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA agent preparation includes two or more iRNA agent(s), e.g., two or more iRNA agents that can mediate RNAi with respect to the same gene, or different alleles of the gene, or with respect to different genes. Such preparations can include at least three, five, ten, twenty, fifty, or a hundred or more different iRNA agent species. Such iRNA agents can mediate RNAi with respect to a similar number of different genes.

Where the two or more iRNA agents in such preparation target the same gene, they can have target sequences that are non-overlapping and non-adjacent, or the target sequences may be overlapping or adjacent.

6 Disorders Associated with Bcr-Abl Fusion Expression

An iRNA agent that targets Bcr-Abl fusion, e.g., an iRNA agent described herein, can be used to treat a subject, e.g., a human having or at risk for developing a disease or disorder associated with Bcr-Abl fusion gene expression, e.g., undesirable cell proliferation or cancer, or, more specifically, leukemia.

For example, an iRNA agent that targets Bcr-Abl fusion mRNA can be used to treat disorders associated with undesirable cell proliferation, such as leukemia, e.g., acute myelogenous leukemia (AML), chronic myelogenous leukemia (CML), or acute lymphoblastic leukemia (ALL). The subject can be one who is currently being treated with a cytostatic or cytotoxic agent, one who has been treated with a cytostatic or cytotoxic agent in the past, or one who is unsuited for treatment with a cytostatic or cytotoxic agent.

7 Treatment Methods and Routes of Delivery

A composition that includes an iRNA agent, e.g., an iRNA agent that targets Bcr-Abl fusion, can be delivered to a subject by a variety of routes. Exemplary routes include intrathecal, parenchymal, intravenous, nasal, oral, and ocular delivery. The preferred means of administering the iRNA agents of the present invention is through parenteral administration.

An iRNA agent can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, or intrathecal or intraventricular administration.

The route of delivery can be dependent on the disorder of the patient. In general, the delivery of the iRNA agents of the present invention is done to achieve systemic delivery into the subject. The preferred means of achieving this is through parental administration.

Formulations for parenteral administration may include sterile aqueous solutions which may also contain buffers, diluents and other suitable additives. For intravenous use, the total concentration of solutes should be controlled to render the preparation isotonic.

Administration can be provided by the subject or by another person, e.g., a caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage. An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of iRNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of iRNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Because iRNA agent mediated silencing can persist for several days after administering the iRNA agent composition, in many instances, it is possible to administer the composition with a frequency of less than once per day, or, for some instances, only once for the entire therapeutic regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of body weight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.001 g to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. It will also be appreciated that the effective dosage of an iRNA agent such as an siRNA used for treatment may increase or decrease over the course of a particular treatment. Changes in dosage may result and become apparent from the results of diagnostic assays. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models as described above.

The invention is further illustrated by the following examples, which should not be construed as further limiting.

EXAMPLES

Source of Reagents

Where the source of a reagent is not specifically given herein, such reagent may be obtained from any supplier of reagents for molecular biology at a quality/purity standard for application in molecular biology.

Example 1 siRNA Synthesis siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Glen Research, Sterling Va.) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification by anion exchange HPLC of the crude oligoribonucleotides were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The purified RNA solution was stored at −20° C. until use.

Example 2

Inhibition of Bcr-Abl Expression in Cells Expressing Bcr-Abl Breakpoint Variants Nucleic acid sequences are represented below using standard nomenclature, and specifically the abbreviations of Table 2.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| Y, y | pyrimidine (C or T, c or u) |
| R, r | purine (A or G, a or g) |
| N, n | any (G, A, C, or T, g, a, c or u) |
| *A,C,G,T,U,a,c,g,t,u* | bold italic: 2'-deoxy-adenosine, 2'-deoxy-cytidine, 2'-deoxy-guanosine, 2'-deoxy-thymidine, 2'-deoxy-uridine, adenosine, cytidine, guanosine, thymidine, uridine (5'-hydroxyl) |

[a]capital letters represent 2'-deoxyribonucleotides(DNA), lower case letters represent ribonucleotides (RNA)

TABLE 3

Nucleic acid sequences of siRNA duplexes targeting Bcr-Abl

| SEQ. ID No. | Sequence sense strand[a,b] | SEQ. ID No. | Sequence antisense strand[a,b] | Duplex descriptor | Specific for Bcr-Abl fusion gene variant |
|---|---|---|---|---|---|
| 1 | cagaguucaa\|aagcccuucag | 23 | cugaagggcuu\|uugaacucugcu | BAF7 | Bcr-Abl-e14a2 |
| 3 | caguguucau\|aagccguucag | 4 | cugaacggcuu\|augaacacugcu | BAF8 | Bcr-Abl-e14a2, mismatch to BAF7[c] |
| 5 | agaguucaa\|aagcccuucagc | 24 | gcugaagggcuu\|uugaacucugc | BAF9 | Bcr-Abl-e14a2 |
| 7 | cagaguugaa\|aagcccuucag | 8 | cugaagggcuu\|uucaacucugcu | BAF1 | Bcr-Abl-e14a2, mismatch to BAF7[d] |
| 9 | uaaggaag\|aagcccuucagcg | 10 | cgcugaagggcuu\|cuuccuuauu | BAF3 | Bcr-Abl-e13a2 |
| 11 | aauaaggaag\|aagcccuucag | 25 | cugaagggcuu\|cuuccuuauuga | BAF15 | Bcr-Abl-e13a2 |
| 13 | ggaag\|aagcccuucagcggcc | 26 | ggccgcugaagggcuu\|cuuccuu | BAF17 | Bcr-Abl-e13a2 |
| 15 | aucaauaaggaag\|aagcccuu | 27 | aagggcuu\|cuuccuuauugaugg | BAF19 | Bcr-Abl-e13a2 |
| 17 | aucuauaagcaag\|aaccccuu | 18 | aaggguu\|cuugcuuauagaugg | BAF28 | Bcr-Abl-e13a2, mismatch to BAF19[e] |
| 19 | ggagacgcag\|aagcccuucag | 28 | cugaagggcuu\|cugcgucccau | BAF22 | Bcr-Abl-e1a2 |
| 21 | gacgcag\|aagcccuucagcgg | 22 | ccgcugaagggcuu\|cugcgucuc | BAF24 | Bcr-Abl-e1a2 |

[a]See Table 2 for an explanation of nucleotide representation (e.g., lower case letters, bold and italicized letters).
[b]exact Bcr-Abl fusion site is marked by vertical line
[c]Pos. 4 a => u, Pos. 10 a => u, Pos. 16 c => g in sense strand
[d]Pos. 16 c => g in sense strand
[e]Pos. 4 a => u, Pos. 10 c => g, Pos. 16 g => c in sense strand Table 3 lists the nucleic acid sequences of siRNAs specific for Bcr-Abl fusion variants Bcr-Abl-e14a2, Bcr-Abl-e13a2, and Bcr-Abl-e1a2 which were synthesized.

The exact fusion site of the Bcr and Abl sequences on the Bcr-Abl mRNA represents a leukemia specific nucleotide sequence. Such fusion transcripts encoding disease specific proteins are ideal targets for a tumor-specific RNAi approach. The aim of the present study was to develop an optimized in vitro Bcr-Abl RNAi protocol. Therefore, several chemically synthesized asymmetric siRNAs, as well as stable expressed shRNAs targeting the fusion site of the clinically relevant Bcr-Abl transcript variants (e14a2, e13a2 or e1a2) were evaluated. RNAi efficiency was determined mainly by Western blot analysis of the Bcr-Abl protein level and by assessing the impact on the leukemic growth of the treated cells.

The results of this work show that repeated transfection with chemically synthesized 21 nt (sense strand) –23 nt (antisense strand) siRNAs at intervals of 24 h was much more effective for both down-regulation of the Bcr-Abl protein and induction of cell death: A single treatment of 32Dp210/e14a2 with the Bcr-Abl-e14a2 specific siRNA BAF7 resulted in a notable reduction of Bcr-Abl protein levels followed by a decrease in the viability of 32Dp210/e14a2 cells to approximately 59% relative to electroporation control cells (EPC, 100%). By contrast, four consecutive treatments of cells with BAF7 reduced the amount of Bcr-Abl protein to the detection limit and led to a virtual loss of viability. Similar conclusions were reached by determination of total cell numbers 48 h following last treatment: whereas the number of cells transfected with mismatched control siRNA (BAF8) increased from 2.5 Mio cells to more than 25 Mio cells within 48 h, a single transfection with BAF7 was sufficient to reduce proliferation by approximately 40% and repeating the treatment four times with the Bcr-Abl specific BAF7 siRNA, resulted in a greater than 90% inhibition of the increase in cell number.

The observation that prolonged exposure notably increased the efficiency of siRNAs may be at least partially explained by the long half life of Bcr-Abl. For example, Spiller and colleagues (Spiller D G, et al., Antisense Nucleic Acid Drug Dev. 1998, 8:281) determined the half life of p210Bcr-Abl (e13a2) in human KYO-1 cells as >48 h. The target protein half life was shown to be important for the effectiveness of conventional antisense—(as)—oligodesoxynucleotides (ODN): p210Bcr-Abl (e13a2) protein levels were unaffected by treatment with an as-ODN targeted to Bcr-Abl-e13a2 mRNA, even though mRNA levels were substantially reduced at early time points. Secondly, the target gene down-regulating effect of siRNAs achieved in mammalian cells is generally transient (for review: Mittal V, Nat Rev Genet. 2004, 5:355). Accordingly, Bcr-Abl protein levels recovered within 48 h after the last siRNA treatment in the cell lines used in this work. But the results of the present work show that this limitation can be overcome, either by repeated treatment with chemically synthesized siRNA at intervals of 24 h or by stable shRNA expression. With this optimized protocol the decrease in Bcr-Abl protein levels achieved was up to 86%, accompanied by a loss of viability of up to 96%.

To assess whether RNAi dependent inactivation of Bcr-Abl leads to sensitization of Bcr-Abl expressing cells to clinical therapeutics, the sensitivity to imatinib and γ-irradiation was determined following repeated treatment of 32Dp210/e14a2 cells with anti-Bcr-Abl siRNA. It could be shown that interference with Bcr-Abl expression is capable to enhance the sensitivity of the cells for both γ-irradiation and imatinib mesylate.

The γ-irradiation dose causing a 50% cell kill was 2.5 Gy in 32Dp210/e14a2 cells treated with Bcr-Abl homologous siRNA, whereas cells treated with mismatch control tolerated approximately 2.5 times higher doses (6 Gy). The quantity of Bcr-Abl protein also determined the sensitivity of these cells to imatinib mesylate. After reduction of the Bcr-Abl protein level with siRNA a 3.4 fold drop of the IC50 of imatinib mesylate was observed in 32Dp210/e14a2 cells when compared to controls. This phenomenon was also observed in human M07p210/e14a2 cells: 0.05 µM imatinib mesylate caused a significant induction of apoptosis in BAF7-treated cells whereas the same concentration had no considerable effect on electroporation control cells.

These results are in disagreement with some of the previously published data, where no additive effect on the induction of apoptosis was observed in K562 cells upon co-treatment with imatinib mesylate and an siRNA agent specific for Bcr-Abl (Wilda M, et al., Oncogene. 2002, 21:5716). The K562 cells employed by Wilda et al., supra, exhibited a very high level of resistance to imatinib mesylate as evidenced by the fact that only 8% underwent apoptosis after a 48 h treatment with imatinib mesylate alone. Such a highly resistant cell system may be suboptimal for evaluating possible additive effects with other potential inhibitors. By contrast, results corroborating our findings were published recently by Chen and colleagues (Chen J, et al., J Clin Invest. 2004, 113:1784), illustrating that the down-regulation of the fusion protein TEL-PDGFβR by RNA interference sensitizes TEL-PDGFβR expressing cells for imatinib mesylate and rapamycin, hence antagonizing drug-resistance. As breakpoint specific siRNAs have to overlap the breakpoint on either side, only a limited number of approximately 10 different potential siRNA sequences may be chosen for RNAi directed silencing of fusion sequences.

Additionally, siRNA treatment restored imatinib sensitivity in cells expressing the imatinib resistance conferring Bcr-Abl variant H396P: Two of the imatinib resistance causing Bcr-Abl variants found in leukemia patients who relapsed after initial response to imatinib are Bcr-Abl -T315I and Bcr-Abl-H396P. These proteins display a single amino acid change in their kinase domain compared to Bcr-Abl (wt) rendering them less accessible to imatinib. Accordingly, expression of Bcr-Abl-T315I in 32D cells conferred complete resistance to imatinib mesylate and expression of Bcr-Abl-H396P rendered the respective cells ~4.7 fold less sensitive to imatinib mesylate when compared to 32Dp210-wt. siRNA treatment led to a significant downregulation of Bcr-Abl in all 3 cell lines. This down-regulation of Bcr-Abl protein levels using siRNA agents resulted in a 3.4 fold sensitization of 32Dp210 wt and a 4 fold sensitization of 32Dp210-H396P to imatinib mesylate. By contrast, imatinib mesylate sensitivity of 32Dp210-T315I cells highly resistant to imatinib mesylate was not significantly affected by siRNA treatment, presumably for the same reason as given above for the lack of a significant effect as observed by Wilda et al., Further, Corbin et al. showed that the T315I-mutated Abl kinase domain exhibited no significant inhibition at imatinib concentrations 200-fold higher than the IC50 value of the WT kinase; it also showed a 2-fold increase in its ATP affinity relative to the wild type protein (Corbin A S, Buchdunger E, Furet P, Druker B J. Analysis of the structural basis of specificity of the Abl kinase by STI571. J Biol Chem 2001; 277: 32214-9.). supra: The effect of imatinib treatment in 32Dp210T315I is itself too small to observe an increased imatinib sensitivity mediated by siRNA treatment.

Any off-target siRNA effects leading to concomitant down-regulation of the physiological c-Abl and Bcr gene expression were excluded in the present study. The great specificity of the RNAi effect was confirmed by the fact that even a single point mutation in the siRNA sequence led to significant loss of siRNA efficacy. Also, siRNAs targeting the breakpoint variants e13a2 and e14a2 affected only their respective target RNAs but not other breakpoint variants sharing the same a2 portion. This strongly supports the view that fusion genes resulting from translocations can be specifically targeted by RNAi. Still, predicting the effectiveness of siRNA molecules appears to be difficult. The target regions of the different siRNAs used in this work exhibited considerable overlap. Yet, siRNA efficiency varied extremely. For example, the target sequence of the Bcr-Abl -e13a2 specific siRNA BAF3 was shifted only 2 nt downstream into the Abl part of the fusion site compared to BAF15. Nevertheless, in contrast to BAF15, BAF3 was completely ineffective. The same was true for the Bcr-Abl-e1a2 specific siRNAs BAF22 and BAF24. The sequence of BAF24 was quite similar to that of BAF22, shifted only by 3 nt further into the Abl region of the fusion transcript. BAF22 actively silenced Bcr-Abl-e1a2 gene expression whereas BAF24 did not. Overall, these results show that the efficiency of siRNAs targeted at the breakpoint sites in oncogenic fusion proteins may not be predicted.

TABLE 4

Cell lines used in determination of siRNA activity

| Cell line | Description | Bcr-Abl expression |
|---|---|---|
| 32D | murine bone marrow; DSMZ-Nr.: ACC 411 | — |
| 32Dp210-wt bzw. 32Dp210/e14a2 | generated by transfection of 32D-cells with retroviral vector Migp210-wta (Pear WS, et al.,. Blood. 1998, 92: 3780) | + (e14a2) |
| 32Dp210-T315I | generated by transfection of 32D-cells with retroviral vector Migp210-T315Ia (v. Bubnoff N, et al., Lancet. 2002, 359: 487) | + (e14a2) |
| 32Dp210-H396P | generated by transfection of 32D-cells with retroviral vector Migp210-H396Pa (v. Bubnoff et al., Lancet. 2002, 359: 487) | + (e14a2) |
| 32Dp210/e13a2 | generated by transfection of 32D-cells with retroviral vector pSRβMSVtkneo-p210/e13a2b (Muller AJ, et al., Mol Cell Biol. 1991;11: 1785) | + (e13a2) |
| 32Dp190/e1a2 | generated by transfection of 32D-cells with retroviral vector pSRβMSVtkneo-p190/e1a2d (Muller AJ, et al., Mol Cell Biol. 1991;11: 1785) | + (e1a2) |
| M07p210/e14a2 | generated by transfection of M07-cells with retroviral vector pGD210 (Daley GQ, et al., Science 1990; 247: 824) | + (e14a2) |
| K562 | human CML-blast cells, DSMZ-Nr.: ACC 10 | Ph+ (e14a2) |
| MEG-01 | human CML-blast cells (megakaryocytic), DSMZ-Nr.: ACC 364 | Ph+ (e13a2) |
| SUP-B15 | human B cell precursor leukemia cell line; DSMZ-Nr.: ACC 389 | Ph+ (e1a2) |

(DSMZ: Deutsche Sammlung für M und Zelllinien)

Cells were cultivated in RPMI/10% FCS complemented with glutamine and Penicillin/Streptomycin. Primary CD34 positive cells were grown in RPMI medium supplemented with glutamine, Penicillin/Streptomycin, 20% FCS, recombinant human IL-3 (10 ng/ml), human G-CSF (20 ng/ml), and human FLT3 (100 ng/ml).

Protein assay: Western blot analysis was performed ~24 h following the last siRNA -treatment or ~96 hours following transfection with the pSUPER siRNA-expression vector as described (Goetz A W, et al., Cancer Res. 2001, 61:7635)

Survival Assay: Following the last siRNA treatment cells were seeded in 96 well plates and cultivated for another ~48 hours. Cell survival was then measured by MTT assay as described (Van der Kuip H, et al., Blood. 2001, 98:1532)

siRNA-transfection: siRNAs were transfected into the murine cell lines 32Dp210Bcr-Abl-e14a2, -e13a2, 32Dp190Bcr-Abl-e1a2 and the human leukemic cell line MEG-01 using electroporation. Cell density was adjusted to 2.5-5×10$^6$/ml in RPMI/10% FCS. 800 µl of this cell suspension were mixed with siRNA in a 4 mm electroporation cuvette. Cells were electroporated by means of an EasyJect electroporator (peqlab, Erlangen, Germany) using a single-pulse protocol (250 V, 1800 µF, 8.). This treatment was repeated in intervals of 24 hours as indicated.

All cell lines used exhibit strict dependency on the activity of Bcr-Abl. In 32Dp210Bcr-Abl-e14a2, -e13a2 and 32Dp190Bcr-Abl-e1a2 inhibition of Bcr-Abl can be compensated by addition of exogenous growth factor to the medium. Therefor, recombinant murine IL-3, (1 ng/ml) was added to the growth medium during siRNA treatment of these cell lines. Following the last siRNA treatment cells were washed and factor deprived before starting the different examination procedures (Western blot/MTT).

For the transfection of siRNA molecules into the human K562 cells we used Lipofectamin™ 2000 (Invitrogen, Karlsruhe). 1.5 Mio. cells were plated in 1.5 ml RPMI/10% FCS w/o antibiotics into a 6 well plate. For each well 500 µl transfection solution was prepared, containing 8.4 µg siRNA and 21 µl Lipofectamin in OPTI-MEM I reduced serum medium (Gibco, Karlsruhe). The cells were incubated 5 hours with the transfection solution, then the medium was changed to RPMI/10% FCS complemented with Penicillin/Streptomycin. When treated several times, cells were counted ~24 h following treatment, diluted to 1 Mio/ml and seeded again in a 6 well plate (1.5 ml cell suspension per well). Transfection was then repeated exactly as the day before.

We used three murine hematopoetic 32D cell lines expressing either p210Bcr-Abl (e14a2), p210Bcr-Abl (e13a2) or p190Bcr-Abl (e1a2) to study the effectiveness of siRNAs to silence each of these human Bcr-Abl fusion breakpoint variants. In addition, experiments were performed in human Ph+leukemia cells (K562, MEG-01). All siRNAs used were directed to breakpoints of the Bcr and Abl sequence of the respective Bcr-Abl mRNA. RNAi-efficiency was assayed via analysis of Bcr-Abl protein levels and by monitoring the biological effect using MTT viability assay.

Figure 2A:
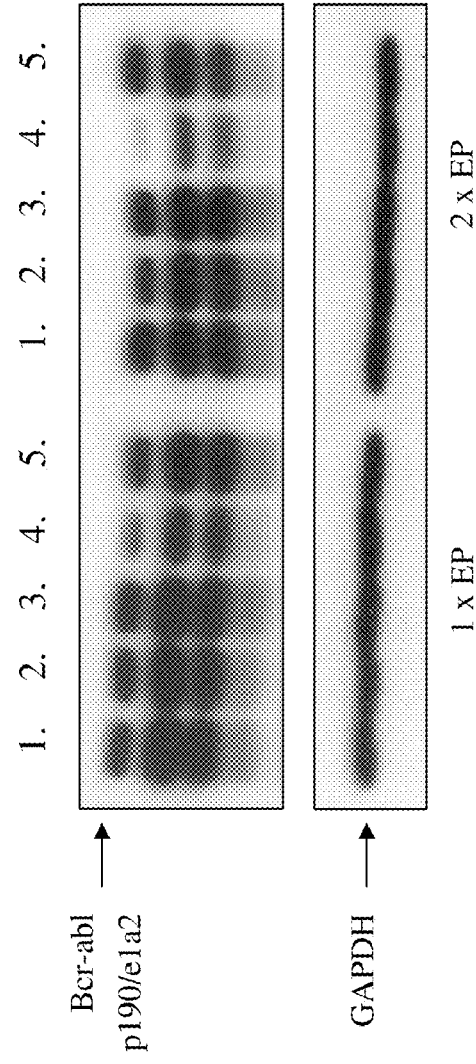
FIGS. 2A-2B: ~5 Mio 32Dp190/e1a2 cells have been electroporated twice at intervals of 24 h with the indicated siRNA. BAF22/BAF24: bcr-abl-e1a2-specific siRNAs; BAF9: bcr-abl-e14a2-specific siRNA, served as control; BAF19: bcr-abl-e13a2-specific siRNA, served as control; EPC: electroporation control.
Figure 2B:
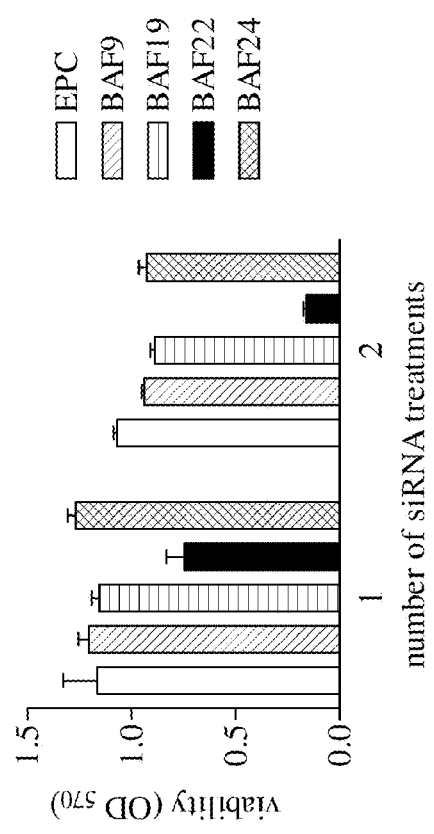

In order to determine optimal conditions for RNA interference, we repeated the siRNA treatment one to four times at intervals of 24 hours. One single treatment of 32Dp210Bcr-Abl (e14a2) with the Bcr-Abl-e14a2 specific siRNA BAF7 resulted in a significant reduction of Bcr-Abl protein levels. However, Bcr-Abl protein levels quickly recovered to pre-treatment levels. Despite its short duration, the effect was still sufficient to reduce the viability of cells to approximately 59% relative to control cells (EPC, 100%). Repeated treatment was much more effective both for down-regulation of the Bcr-Abl protein and inducing cell death: Fourfold BAF-7 treatment of cells resulted in almost complete disappearance of Bcr-Abl protein and led to virtually complete loss of viability. The residual viability level of the cells treated four times with BAF7 measured in MTT assay was not more than ~2.5% of the level of the control cells. Identical results were obtained when cell counts 48 hours following last treatment were used for assessment of the biological effect. Both mock-treated and cells treated with a mismatch siRNA still increased their cell number from 2.5 Mio cells to more than 25 Mio cells within 48 hours. Cells transfected once with siRNA homologous to Bcr-Abl-e14a2 (BAF7) reduced proliferation by app. 40%. Repeating treatment two or four times with the Bcr-Abl specific BAF7 siRNA more effectively reduced Bcr-Abl dependent cell growth reaching a growth inhibition of more than 90%. In addition we could show in these 32Dp210Bcr-Abl (e14a2) cells, that a single point mutation in the siRNA sequence is capable to impair the silencing effect. We used a siRNA molecule with a single mismatch compared to BAF7 (BAF1). Treatment with BAF1 resulted in a less efficient down-regulation of Bcr-Abl protein levels compared to treatment with the breakpoint specific siRNA (BAF7) in 32Dp210Bcr-Abl (e14a2) cells (FIG. 2A). The lower efficiency of BAF1 became even more obvious when the biological effect of BAF1 was assessed. Even cells treated four times with BAF1 showed only a moderate reduction in viability to 52% respective to EPC. This magnitude was comparable to the effect of a single treatment with the optimal siRNA.

We confirmed the observation that prolonged siRNA treatment is more effective for RNA interference by studying the biological effect of BAF7 in human K562 cells. Since the K562 cells proved to be more sensitive to our electroporation protocol, cells were transfected using lipofectamin 2000. 48 hours following one single treatment with siRNA cells showed only a minimal growth reduction. In contrast, 48 hours following the third lipofection with siRNAs at intervals of 24 hours viability was significantly reduced to 45% in cells treated with siRNA homologous to Bcr-Abl-e14a2 mRNA (BAF7).

All three major Bcr-Abl oncogene variants -e14a2, -e13a2 and -e1a2 can be targeted by RNA interference. To identify effective siRNAs for inhibition of the second major Bcr-Abl fusion gene relevant in CML, Bcr-Abl-e13a2, we treated 32Dp210Bcr-Abl (e13a2) cells with four siRNAs (BAF3, BAF15, BAF17, BAF19) targeting different sequences of the Bcr-Able13a2 mRNA breakpoint. As a control we used a siRNA directed to the Bcr-Abl-e14a2 fusion sequence (BAF9). BAF3, BAF15, BAF17 and BAF19 exhibited significantly different efficiencies in down-regulating Bcr-Abl. Repeated electroporation of the siRNAs BAF15 and BAF19 led to effective down-regulation of Bcr-Abl protein levels. Despite the considerable overlap in their target sequence, BAF17 and BAF3 had no effect Bcr-Abl protein levels. Equivalent results were obtained when studying the biological effect of these siRNAs via the MTT-viability assay. Three treatments of 32Dp210Bcr-Abl (e13a2) cells with the effective siRNAs BAF15 and BAF19 resulted in an almost complete loss of viability. 48 h following 3rd treatment viability was only ~10% (BAF15) and ~14% (BAF19) of controls (EPC). Hence, siRNAs that were ineffective in down-regulating Bcr-Abl protein levels, BAF3 and BAF17, did also not interfere with the viability of the cells. Using the same protocol, siRNA BAF19 effectively silenced Bcr-Abl-e13a2 expression in the cell line MEG-01, a human megakaryocytic CML cell line expressing the Bcr-Abl-e13a2 RNA. When treated three times with the Bcr-Able13a2-specific siRNA BAF19 the cells showed a significant loss of Bcr-Abl protein levels compared to cells that were electroporated with the respective mismatch control (BAF28). Down-regulation of Bcr-Abl protein levels by RNAi also caused substantial loss of viability in MEG-01 cells. In MEG-01 cells treated three times with the effective BAF19 siRNA viability was reduced to a level of ~28% compared to the level in control cells (EPC, 100%).

The third major Bcr-Abl variant, p190Bcr-Abl (e1a2) can be detected in 20-50% of the Ph+patients with adult-ALL and in approximately 90% of the patients with Ph+pediatric ALL. To asses whether this Bcr-Abl fusion site may also serve as a target for RNAi, we treated 32Dp190Bcr-Abl (e1a2) cells twice with two different sequence specific siRNAs (BAF22, BAF24). As controls we used active siRNAs directed to Bcr-Abl-e14a2 (BAF9) and Bcr-Abl-e13a2 (BAF19). Repeated treatment at intervals of 24 h led to significant down-regulation of Bcr-Abl protein levels only in cells treated with the siRNA BAF22. Transfection of the BAF24 siRNA had no effect at all. In 32Dp190Bcr-Abl (e1a2) effective reduction of Bcr-Abl Protein levels after 2nd treatment with BAF22 siRNA resulted in a reduction of viability reaching al level of 15% compared to EPC (100%).

siRNA BAF22 also effectively silenced Bcr-Abl-e1a2 expression in the cell line SUP-B15, human B cell precursor leukemia cell line expressing the Bcr-Abl-e1a2 RNA. The human B cell precursor leukemia cell line SUP-B15 was originally established from the bone marrow of a 9-year-old boy with acute lymphoblastic leukemia (B cell precursor ALL) and carries the ALL variant (m-bcr) of the Bcr-Abl fusion gene (e1a2). This cell line was obtained from the DSMZ cell culture collection (ACC 389; DSMZ, Braunschweig).

Figure 3:
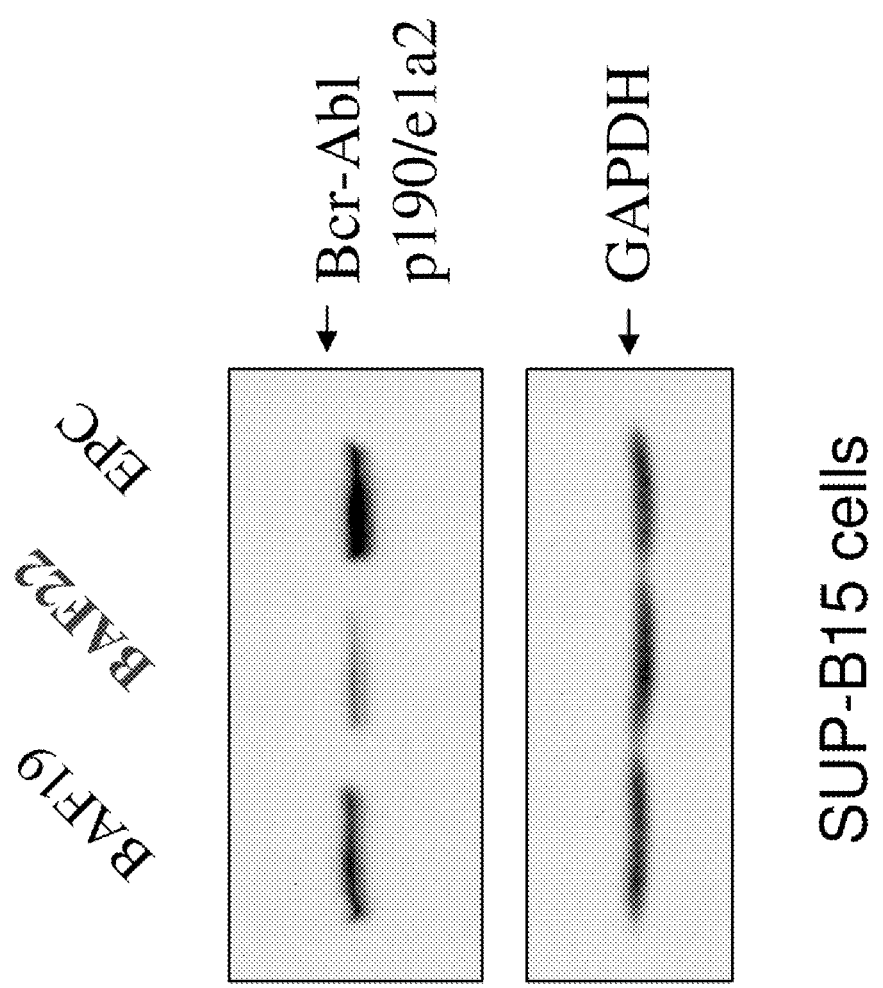
FIG. 3: Cells from the human B cell precursor leukemia cell line SUP-B15 (ACC 389; DSMZ, Braunschweig, breakpoint variant e1a2) were treated as described for FIG. 3 with an e1a2-specific siRNA (BAF22) or with siRNA directed to another breakpoint variant (BAF19, specific for e13a2) as a control. BAF22 treatment at intervals of 24 hours for 3 times led to significantly reduced p190Bcr-Abl protein levels compared to the electroporation-control (EPC) or to the BAF19 control.

SUP-B15 cells were treated by electroporation as described above with an e1a2-specific siRNA (BAF22) or with siRNA directed to another breakpoint variant (BAF19) as a control. BAF22 treatment at intervals of 24 hours for 3 times led to significantly reduced p190Bcr-Abl protein levels compared to the electroporation-control (EPC) or to the BAF19 control (See FIG. 3).

The tendency that prolonged siRNA treatment is more effective in terms of RNAi was also observed in the 32Dp210Bcr-Abl (e13a2) and 32Dp190Bcr-Abl (e1a2) cell lines. Repeated electroporation of siRNAs at an interval of 24 hours) was necessary to achieve a distinct down-regulation of Bcr-Abl protein levels and led to further loss of viability than single treatment.

We have therefore proven that the expression of all major Bcr-Abl breakpoint variants may be influenced by siRNA treatment of cells in vitro. Testing a panel of siRNA molecules we were able to identify effective siRNAs for the e14a2, the e13a2 and the e1a2 breakpoint variants. These data extend previous experiments published by others and by our group on the down-regulation of Bcr-Abl transcripts bearing the e14a2 fusion.

Example 3

Bcr-Abl Down-regulation in Cells Isolated from Human Leukemia Patients

Down-Regulation of Bcr-Abl in Primary Patient Cells Positive for Breakpoint Variant e14a2

CD34 positive cells were isolated from 3 newly diagnosed and untreated Philadelphia chromosome-positive CML patients in chronic phase. Informed consent was obtained by the patients prior to collection of cells. Mononuclear cells were harvested by Ficoll-Hypaque density gradient centrifugation (Seromed, Berlin, Germany). CD34 positive cells were isolated using a stem cell isolation kit and a MACS column (Miltenyi Biotech, Bergisch Gladbach, Germany) according to manufacturer's instructions. Cell purity was checked by FACS analysis using a FITC-conjugated anti-CD34 antibody (BD Biosciences, Immunocytometry Systems, San Jose, Calif., USA). The fraction of CD34 positive cells ranged from 96 to 99%.

CD34 positive cells were grown to a density of 500,000 cells/ml in RPMI medium supplemented with 20% FCS, recombinant human IL-3 (10 ng/ml, Stratmann Biotech AG, Hamburg, Germany), human G-CSF (20 ng/ml, Amgen, Munich, Germany), and human recombinant FLT3 ligand (100 ng/ml, Research Diagnostics Inc., Concord Mass., USA). A small aliquot of the cells was used for determining the Bcr-Abl breakpoint variant prior to siRNA treatment. Total RNA was isolated using the RNeasy-Mini Kit (Qiagen, Hilden, Germany) according to manufacturer's instructions and 1 µg RNA was used to generate cDNA using SuperScript reverse transcriptase (Gibco-BRL, Carlsbad Calif., USA) according to the manufacturer's protocol. One microliter of cDNA was then used for PCR with the breakpoint specific Bcr-Abl primers 5'-Bcr-Abl (5'-CTGACATCCGTG-GAGCTG-3' (SEQ ID NO:29)) and 3'-Bcr-Abl (5'-CAT-TGTGATTATAGCCTAAGA-3' (SEQ ID NO:30)) generating a 390 bp fragment (e14a2) or a 290 bp fragment (e13a2).

On day 2 of cell culture, cells were treated with siRNA. Cells were diluted to a density of $2.5 \times 10^6$ in 800 µl growth medium and mixed with 12.8 µl of a 50 µM solution of the respective siRNA in annealing buffer (20 mM NaPO4, 100 mM NaCl; pH 6.9) in a 4-mm electroporation cuvette. The cells were then electroporated using an EasyJect-electroporator, single pulse protocol (250V, 1800 µF). This treatment was repeated after 24 hours. After the second treatment, the cells were washed and factor deprived. Following a further cultivation period of 24 hours, the cells were harvested for western blot analysis.

Figure 4:
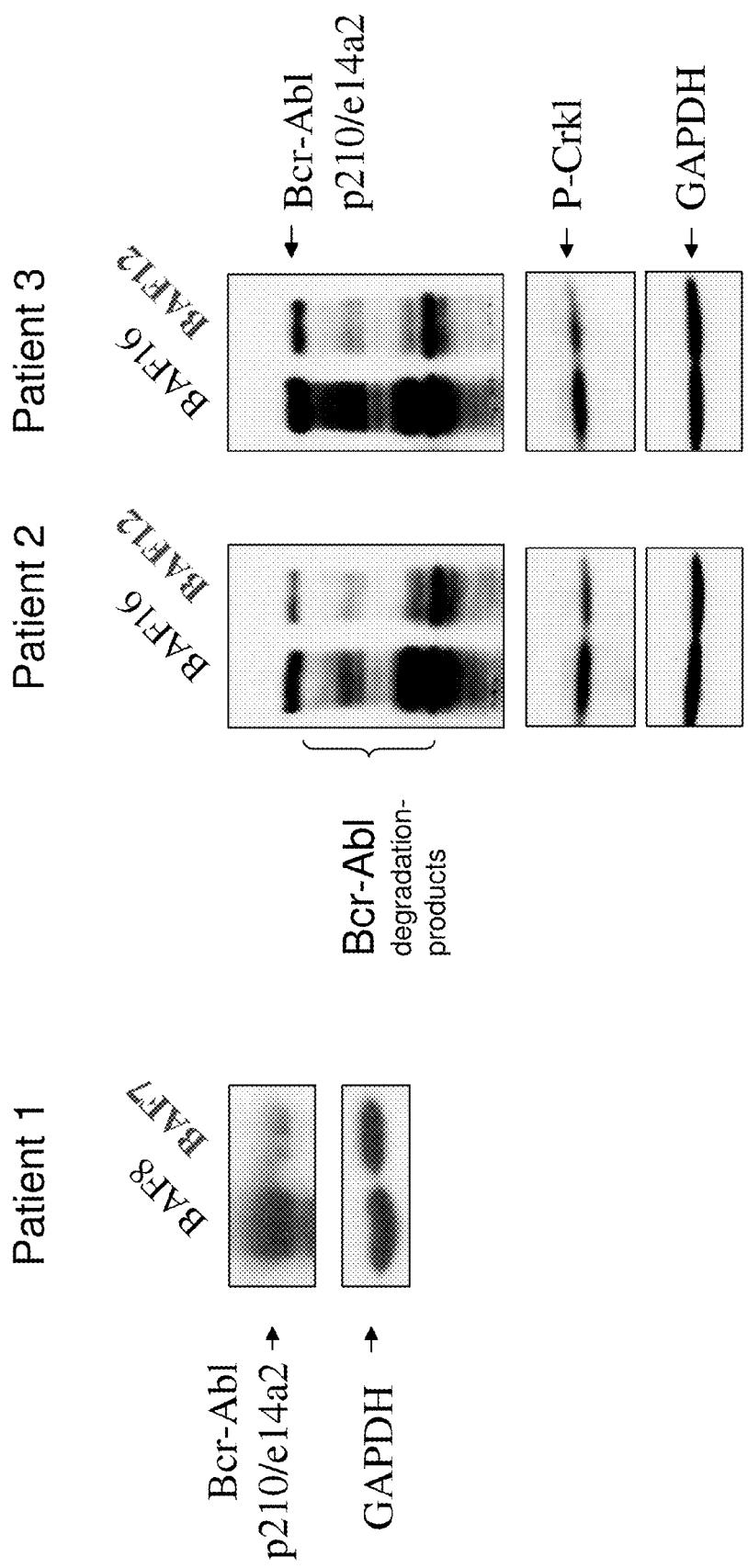
FIG. 4: CD34 positive cells isolated from 3 newly diagnosed and untreated Philadelphia chromosome-positive CML patients in chronic phase and positive for bcr-abl-e14a2 by Ficoll-Hypaque density gradient centrifugation and affinity column purification were treated with siRNAs BAF7 (e14a2 specific, Patient 1), BAF8 (mismatch control, Patient 1), BAF12 (e14a2 specific, Patient 2+3), and BAF16 (e13a2 specific, Patient 2+3). Cells were diluted to a density of 2.5× 10$^6$ in 800 µl growth medium, mixed with 12.8 µl of a 50 µM solution of the respective siRNA in a 4-mm electroporation cuvette, and electroporated using a single pulse protocol (250V, 1800 µF). This treatment was repeated after 24 hours, the cells were washed, incubated for another 24 hours, and harvested for western blot analysis. BAF7 or BAF12 treatment resulted in a significant reduction of Bcr-Abl protein levels compared to cells treated with the mismatch control (BAF8) or with the siRNA homologous to e13a2 (BAF16). Additionally, BAF12 treatment compromised Bcr-Abl activity. Phosphorylation of CRKL, the direct downstream substrate of Bcr-Abl, was significantly reduced in cells treated with BAF12.

BAF7 or BAF12 (both e14a2-specific) treatment resulted in a significant reduction of Bcr-Abl protein levels compared to cells treated with mismatch control (BAF8) or with siRNA homologous to e13a2 (BAF16). Additionally, BAF12 treatment compromised Bcr-Abl activity. Phosphorylation of CRKL, the direct downstream substrate of Bcr-Abl, was significantly reduced in cells treated with BAF12 (See FIG. 4).

We claim:

1. A ds iRNA agent comprising an antisense strand and a sense strand and a duplex region wherein the antisense strand consists of the nucleotide sequence of SEQ ID NO: 25.

2. The ds iRNA agent of claim 1, wherein the sense strand consists of the nucleotide sequence of SEQ ID NO: 11.

3. The ds iRNA agent of claim 1, wherein the ds iRNA agent significantly reduces the amount of BCR-ABL fusion protein levels present in cultured mammalian cells after incubation with the ds iRNA agent compared to cells which have not been incubated with the ds iRNA agent, wherein the cells are 32Dp210/e14a2, 32Dp210-T315I, 32Dp210-H396P, 32Dp210/e13a2, 32Dp190/e1a2, M07p210/e14a2, K562, MEG-01, or SUP-B15, or wherein the cells have been isolated from a leukemic patient.

4. The ds iRNA agent of claim 1, wherein the duplex region of the iRNA agent is 21 nucleotide pairs in length.

5. The ds iRNA agent of claim 1, comprising a modification that causes the iRNA agent to have increased stability in a biological sample.

6. The ds iRNA agent of claim 5, comprising a phosphorothioate or a 2'-modified nucleotide.

7. The ds iRNA agent of claim 6, comprising at least one 5'-uridine-adenine-3' (5'-ua-3') dinucleotide wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide.

8. The ds iRNA agent of claim 6, wherein the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O-N-methylacetamido (2'-O-NMA).

9. The ds iRNA agent of claim 1, further comprising a nucleotide overhang comprising 1 to 4 unpaired nucleotides.

10. The ds iRNA agent of claim 9, comprising a single overhang of 2 nucleotides at the 3' end of the antisense strand.

11. The ds iRNA agent of claim 9, wherein the nucleotide overhang is at the 3'-end of the antisense strand of the iRNA agent.

12. The ds iRNA agent of claim 1, further comprising a ligand.

13. The ds iRNA agent of claim 12, wherein the ligand is conjugated to the 3'-end of the sense strand of the iRNA agent.

14. A pharmaceutical composition, comprising:
the ds iRNA agent of claim 1, and
a pharmaceutically acceptable carrier.

15. A method of reducing the amount of BCR-ABL RNA in a cell of a subject, comprising contacting the cell with the ds iRNA agent of claim 1.

* * * * *

UNITED STATES PATENT AND TRADEMARK OFFICE
CERTIFICATE OF CORRECTION

| | | |
|---|---|---|
| PATENT NO. | : 7,994,307 B2 | |
| APPLICATION NO. | : 12/510128 | |
| DATED | : August 9, 2011 | |
| INVENTOR(S) | : Philipp Hadwiger et al. | |

It is certified that error appears in the above-identified patent and that said Letters Patent is hereby corrected as shown below:

Col. 44, Line 7
Please insert the following claim after existing claim 15 --16. A cell comprising the ds iRNA agent of claim 1.--

Signed and Sealed this
Twenty-first Day of February, 2012

David J. Kappos
*Director of the United States Patent and Trademark Office*

UNITED STATES PATENT AND TRADEMARK OFFICE
CERTIFICATE OF CORRECTION

PATENT NO. : 7,994,307 B2  
APPLICATION NO. : 12/510128  
DATED : August 9, 2011  
INVENTOR(S) : Philipp Hadwiger et al.

Page 1 of 2

It is certified that error appears in the above-identified patent and that said Letters Patent is hereby corrected as shown below:

Delete the title page and substitute therefor the attached title page showing the corrected number of claims in patent.

Col. 44, Line 7  
Please insert the following claim after existing claim 15 --16. A cell comprising the ds iRNA agent of claim 1.--

This certificate supersedes the Certificate of Correction issued February 21, 2012.

Signed and Sealed this  
Twentieth Day of March, 2012

David J. Kappos  
*Director of the United States Patent and Trademark Office*

(12) United States Patent
Hadwiger et al.

(10) Patent No.: US 7,994,307 B2
(45) Date of Patent: Aug. 9, 2011

(54) RNAI MODULATION OF THE BCR-ABL FUSION GENE AND USES THEREOF

(75) Inventors: Philipp Hadwiger, Altenkunstadt (DE); Hans-Peter Vornlocher, Bayreuth (DE); Heiko Van Der Kuip, Ammerbuch (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/510,128

(22) Filed: Jul. 27, 2009

(65) Prior Publication Data
US 2010/0234446 A1 Sep. 16, 2010

Related U.S. Application Data

(60) Division of application No. 12/171,291, filed on Jul. 10, 2008, now abandoned, which is a continuation of application No. 11/286,624, filed on Nov. 23, 2005, now abandoned.

(60) Provisional application No. 60/632,403, filed on Dec. 1, 2004, provisional application No. 60/630,878, filed on Nov. 24, 2004.

(51) Int. Cl.
*C07H 21/04* (2006.01)
*C07H 21/02* (2006.01)
*A61K 48/00* (2006.01)

(52) U.S. Cl. ............................ 536/24.5; 536/23.1; 514/44

(58) Field of Classification Search ........................ None
See application file for complete search history.

(56) References Cited

U.S. PATENT DOCUMENTS

| | | | |
|---|---|---|---|
| 5,328,470 A | 7/1994 | Nabel et al. | |
| 5,652,222 A * | 7/1997 | Calabretta et al. | 514/44 A |
| 6,107,094 A | 8/2000 | Crooke | |
| 7,196,184 B2 | 3/2007 | Heidenreich et al. | |
| 2003/0130186 A1 | 7/2003 | Vargeese et al. | |
| 2003/0143732 A1 | 7/2003 | Fosnaugh et al. | |
| 2003/0190654 A1 | 10/2003 | Heidenreich et al. | |
| 2004/0259247 A1 | 12/2004 | Tuschl et al. | |
| 2005/0107325 A1 | 5/2005 | Manoharan et al. | |
| 2005/0159381 A1 | 7/2005 | McSwiggen et al. | |
| 2007/0004664 A1 | 1/2007 | McSwiggen et al. | |
| 2007/0031844 A1 | 2/2007 | Khvorova et al. | |

FOREIGN PATENT DOCUMENTS

| | | |
|---|---|---|
| WO | WO 2003/062432 A1 | 7/2003 |
| WO | WO 2003070972 A2 | 8/2003 |
| WO | WO 2004/064737 | 8/2004 |
| WO | WO 2004/080406 | 9/2004 |
| WO | WO 2004/094345 | 11/2004 |
| WO | WO 2005/115481 | 12/2005 |

OTHER PUBLICATIONS

Bertrand et al. (Biochemical and Biophysical Research Communications, 2002, 296, pp. 1000-1004).*

Elbashir et al. (The EMBO Journal, vol. 20, No. 23, pp. 6877-6888, 2001).*

European Search Report for European Patent Application No. EP 09007997.1, Nov. 2, 2009, 6 pages.

Supplementary European Search Report for European Patent Application No. EP 05857009.4, Mar. 23, 2009, 8 pages.

Wohlbold, L., et al., "Repeated application of sequence-specific siRNA molecules leads to an effective downmodulation of all clinically relevant bcr-abl gene variants," Blood, Nov. 2004, p. 165B, Part 2, vol. 104, No. 11 (Abstract).

Smetsers, T., et al., "An antisense Bcr-Abl phosphodiester-tailed methylphosphonate oligonucleotide reduces the growth of chronic myeloid leukaemia patient cells by a non-antisense mechanism" British Journal of Haematology, 1997, vol. 96, No. 2, 1997, pp. 377-381.

Boese, et al. "Mechanistic Insights Aid Computational Short Interfering RNA Design," Methods in Enzymology 392:73-96, 2005.

Reynolds, et al. "Rational RNA Design for RNA Interference," Nature Biotechnology 22:326-330, 2004.

Barnes et al., "Cytogenetic and Molecular Genetic Aspects of Chronic Myeloid Leukaemia" Acta Haematologica 108:180-202 (2002).

Byrom, W.M., et al. "Inducing RNAi with siRNA Cocktails Generated by RNase III" Tech Notes 10 (1), Ambion, Inc., Austin, TX, USA, Mar. (2003).

Castelli et al., A Study of the Interferon Antiviral Mechanism: Apoptosis Activation by the 2-5A System: J. Exp. Med. 186(6):967-972 (1997).

Chen et al., "Stable expression of small interfering RNA sensitizes TEL-PDGF(3R to inhibition with imatinib or rapamycin" J. Clin Invest. 113(12):1784-1791 (2004).

Chen et al., "Gene therapy for brain tumors: regression of experimental gliomas by adenovirus-mediated gene transfer in vivo" Proc. Natl. Acad. Sci. USA 91:3054-3057 (1994).

Corbin et al., "Analysis of the structural basis of specificity of the Abl kinase by STI571" J. Biol. Chem. 277:32214-32219 (2001).

Damm-Welk, C., et al., "Targeting oncogenic fusion genes in leukemias and lymphomas by RNA interference," Semin Cancer Biol., 2003, pp. 283-292, vol. 13.

Dohjima, T., et al., "Small interfering RNAs expressed from a Pol III promoter suppress the EWS/FLI-1 transcript in an Ewing sarcoma cell line," Mol. Ther., 2003, pp. 811-816, vol. 7.

Elbashir et al., "RNA interference is mediated by 21- and 22-nucleotide RNAs" Genes and Dev. 15:188-200 (2001).

Faderl et al., "The Biology and Therapy of Adult Acute Lymphoblastic Leukemia" Cancer (7):1337-1354 (2003).

Fire et al "Potent specific genetic interference by double stranded RNA in *Caenorhabditis elegans*" Nature 391:806-811 (1998)

Goetz et al., "Requirement for Mdm2 in the Survival Effects of Bcr-Abl and Interleukin 3 in Hematopoietic Cells" Cancer Res. 61:7635-7641 (2001).

Heidel, et al., "Lack of interferon response in animals to naked siRNAs" Nature Biotechn 22 (12):1579-1582 (2004).

(Continued)

*Primary Examiner* — Amy Bowman
(74) *Attorney, Agent, or Firm* — Fenwick & West LLP

(57) ABSTRACT

The invention relates to compositions and methods for modulating the expression of Bcr-Abl, and more particularly to the down-regulation of Bcr-Abl mRNA and Bcr-Abl protein levels by oligonucleotides via RNA interference, e.g., chemically modified oligonucleotides.

16 Claims, 4 Drawing Sheets